United States Patent [19]
Barton et al.

[11] Patent Number: 5,328,463
[45] Date of Patent: Jul. 12, 1994

[54] CONTRAST MEDIA AND FLUID INTRODUCTION SYSTEM

[75] Inventors: Thomas J. Barton; Robbin L. Murdoch, both of Glens Falls, N.Y.

[73] Assignee: Namic U.S.A. Corporation, Glens Falls, N.Y.

[21] Appl. No.: 947,660

[22] Filed: Sep. 18, 1992

[51] Int. Cl.$^5$ ............................................. A61M 3/00
[52] U.S. Cl. ................................... 604/83; 604/246; 604/405
[58] Field of Search ............ 604/82, 83, 86, 126, 604/129, 190, 246, 248, 250, 256, 257, 258, 403, 405, 406, 411; 141/27, 286, 330

[56] References Cited

U.S. PATENT DOCUMENTS

| | | | |
|---|---|---|---|
| 1,677,732 | 7/1928 | Schellberg | 604/246 |
| 4,133,314 | 1/1979 | Bloom et al. | 604/405 |
| 4,253,501 | 3/1981 | Ogle | 604/405 |
| 4,257,416 | 3/1981 | Prager | 604/83 |
| 4,259,187 | 3/1981 | De Frank et al. | 604/190 |
| 4,560,378 | 12/1985 | Weiland | 604/250 |
| 4,997,430 | 3/1991 | Van der Heiden et al. | 604/126 |
| 4,998,926 | 3/1991 | Alchas | 604/257 |

Primary Examiner—John D. Yasko
Attorney, Agent, or Firm—Kenyon & Kenyon

[57] ABSTRACT

A fluid delivery apparatus for administering contrast media or other fluids to a patient. The apparatus includes a reusable main supply system, a disposable fluid administration system, and a transfer syringe. The transfer syringe is used to transfer fluid from the main supply system to the fluid administration system. The administration system includes an air valve and filter to allow for complete drainage of the fluid in the fluid administration system while reducing the likelihood of contaminating the fluid.

6 Claims, 4 Drawing Sheets

CONTRAST MEDIA AND FLUID INTRODUCTION SYSTEM

BACKGROUND OF THE INVENTION a. Field of the Invention

This fluid delivery apparatus provides hospital personnel with a safe way to efficiently administer contrast media or other fluids. More particularly, this invention relates to a fluid delivery apparatus which incorporates a reusable main supply system, a disposable transfer means such as a syringe means, and a disposable fluid administration system for the delivery of fluids to a patient which significantly reduces the likelihood of accidental cross-contamination from one patient to another and reduces the need to dispose of unused fluids.

b. Description of the Prior Art

In the medical setting, and particularly in radiology and cardiology, avoiding the accidental contamination of a patient's vascular system is of great importance. The contamination of a patient while administering fluid can result in severe medical complications and even death.

In a typical fluid introduction system a reservoir of contrast media or other fluid is tapped or spiked and the contrast medium or fluid is administered to the patient via a fluid delivery means. Because there is a direct fluid connection with the patient to the reservoir there is a possibility that the reservoir may become contaminated by the patient. In order to avoid the cross-contamination of patients, any contrast media or other fluid remaining in the reservoir after treatment must be discarded regardless of whether a small or a substantial portion of it remains.

Most prior art fluid delivery systems are designed so that the entire system is discarded after use and an entirely new system is utilized for the next patient. A major disadvantage of these systems is that they are expensive and result in a waste of natural resources.

Other prior art fluid delivery systems are designed so that they can be dismantled, sterilized, and used again with other patients. A major disadvantage of these systems is that the equipment may not be properly sterilized or the parts may be lost or damaged. Other disadvantages are the costs for labor, material and equipment associated with sterilizing the equipment.

A major disadvantage of both of these systems is that the unused fluid source must be discarded to prevent contamination from one patient to another. This can result in significant waste because the fluids used in medicine tend to be expensive.

There continues to be a need for an inexpensive fluid delivery system that reduces the waste associated with discarding the unused portion of contrast media or other fluids and the risk of cross-contamination from patient to patient.

OBJECTIVES AND SUMMARY OF THE INVENTION

In view of the shortcomings of the prior art it is an object of the present invention to provide hospital personnel with a safe and economical system for efficiently administering contrast media or other fluids.

It is another object of the present invention to provide a fluid introduction system that provides separate fluid paths to multiple patients.

It is still another object of this invention to provide a system for administering fluids to multiple patients while maintaining sterility of the fluid supply.

The present invention provides an apparatus for supplying a fluid to a patient comprising: (a) a reusable main supply means defining a longitudinal fluid conduit having a distal end and a proximal end, a first fluid inlet means at the proximal end adapted for fluid communication with a fluid source, a first fluid outlet means at the distal end adapted for fluid communication with a syringe means and adapted to form a substantially fluid tight seal with a protective cap, and a first fluid control means for regulating fluid flow between the first fluid inlet means and the first fluid outlet means disposed between the first fluid inlet means and the first fluid outlet means; (b) a disposable fluid administration means defining a longitudinal conduit having a distal end and a proximal end, a second fluid inlet means at the proximal end of the fluid administration means adapted for fluid communication with a syringe means, a second fluid outlet means at the distal end of the fluid administration means adapted for fluid communication with a means for the delivery of fluid to a patient, a second fluid control means for regulating the flow of fluid between the second fluid inlet means and the second fluid outlet means disposed between the second fluid inlet means and the second fluid outlet means, and a filtering means in fluid communication with the second fluid control means; and (c) a disposable syringe means adapted for fluid communication with the first fluid outlet means and the second fluid inlet means.

DETAILED DESCRIPTION OF THE INVENTION

Figure 1:
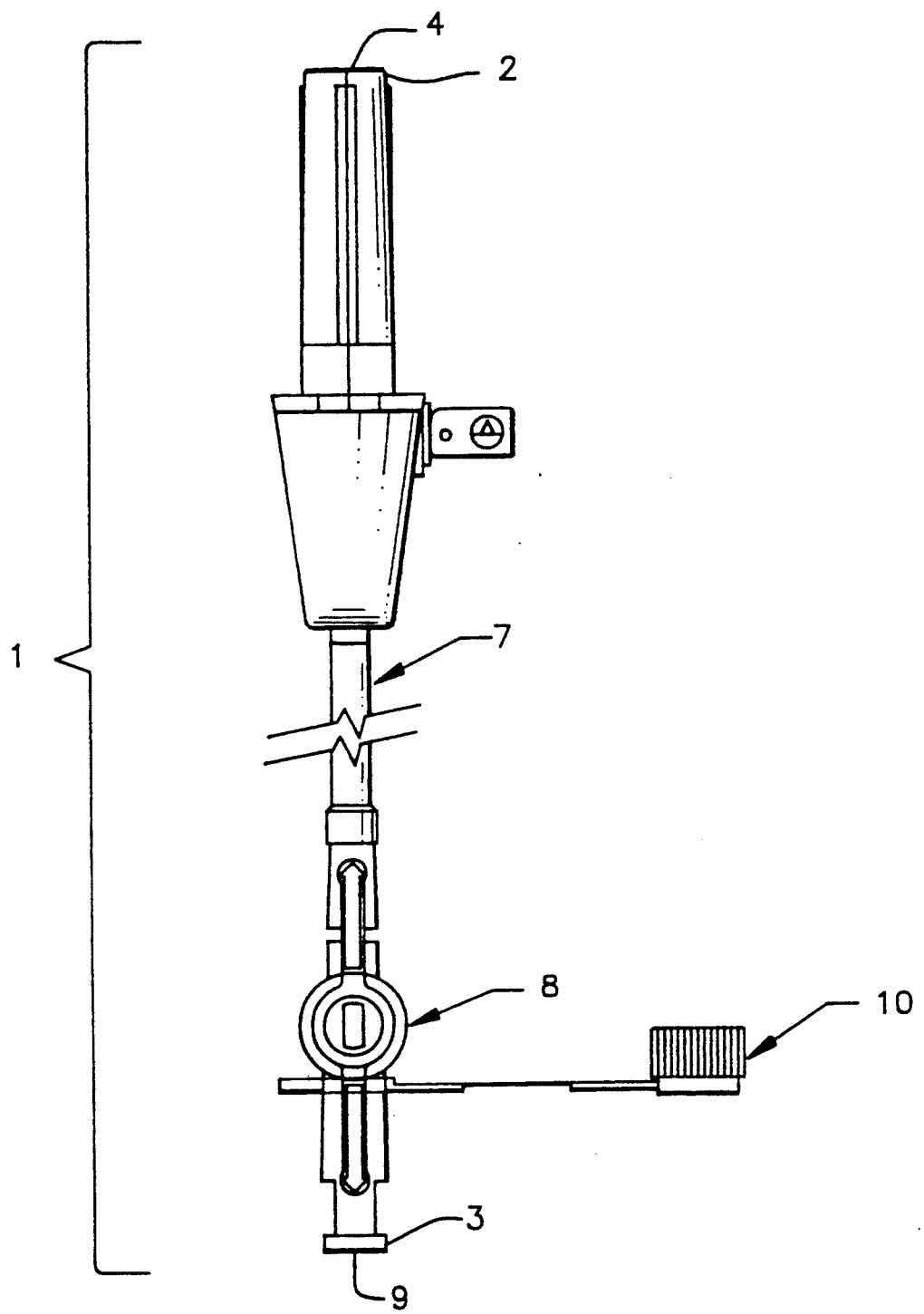
FIG. 1 shows a reusable main supply system constructed in accordance with this invention.

FIG. 1 shows a reusable main supply system 1 having a proximal end 2, a distal end 3, a first fluid inlet means 4, a fluid conduit 7, a first fluid control means 8, a first fluid outlet means 9, and a protective dust cap 10.

Figure 2:
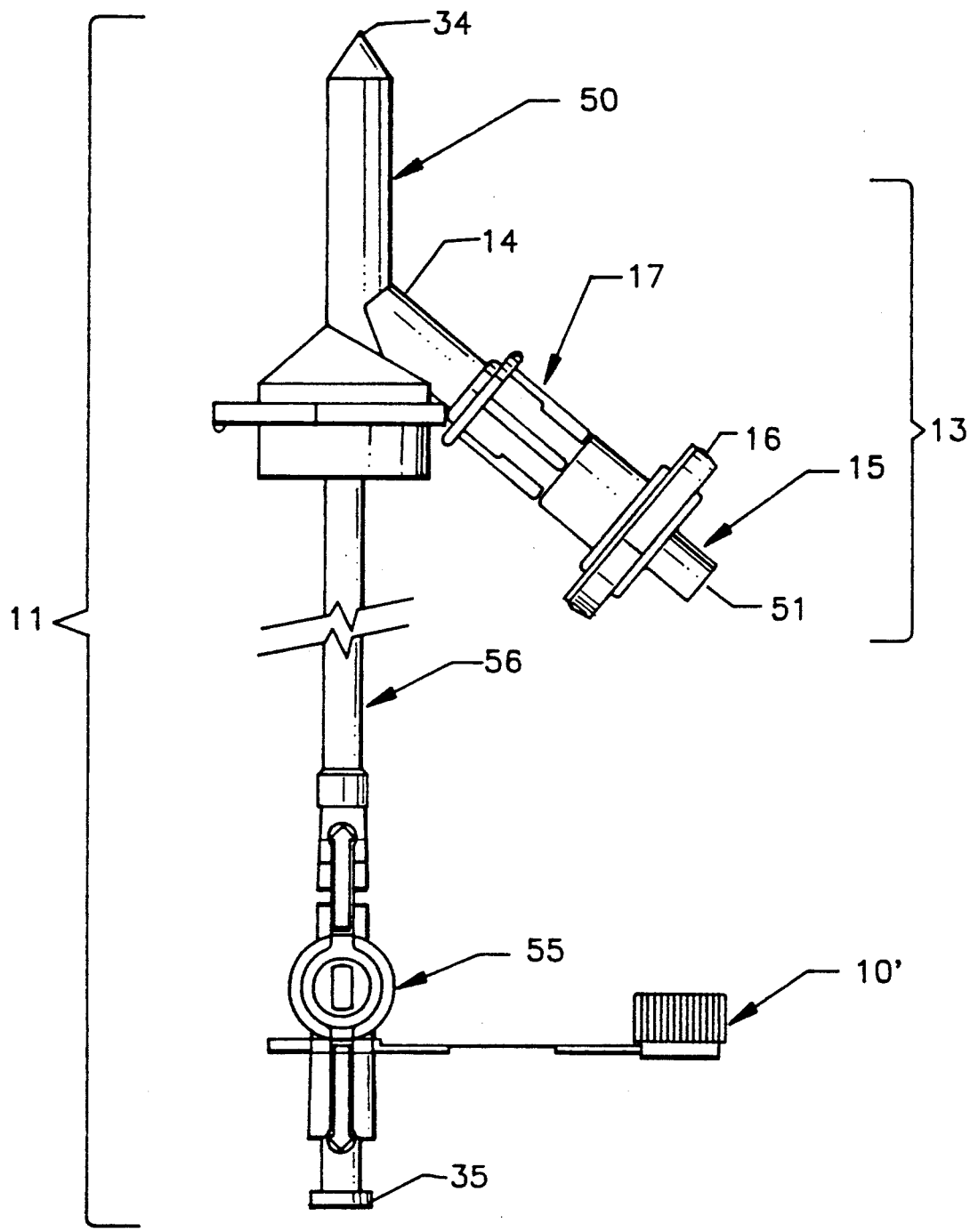
FIG. 2 shows a reusable main supply system constructed in accordance with the invention and adapted to be pressurized.

FIG. 2 shows a reusable pressurizable main supply system 11 having a proximal end 34, a distal end 35, a first fluid inlet means 50, a first fluid control means 55, a fluid conduit 56, a protective dust cap 10', and a pressurization means 13 having a proximal end 14, a distal end 15, a filtering means 16, a check-valve 17, and an air port 51.

Figure 3:
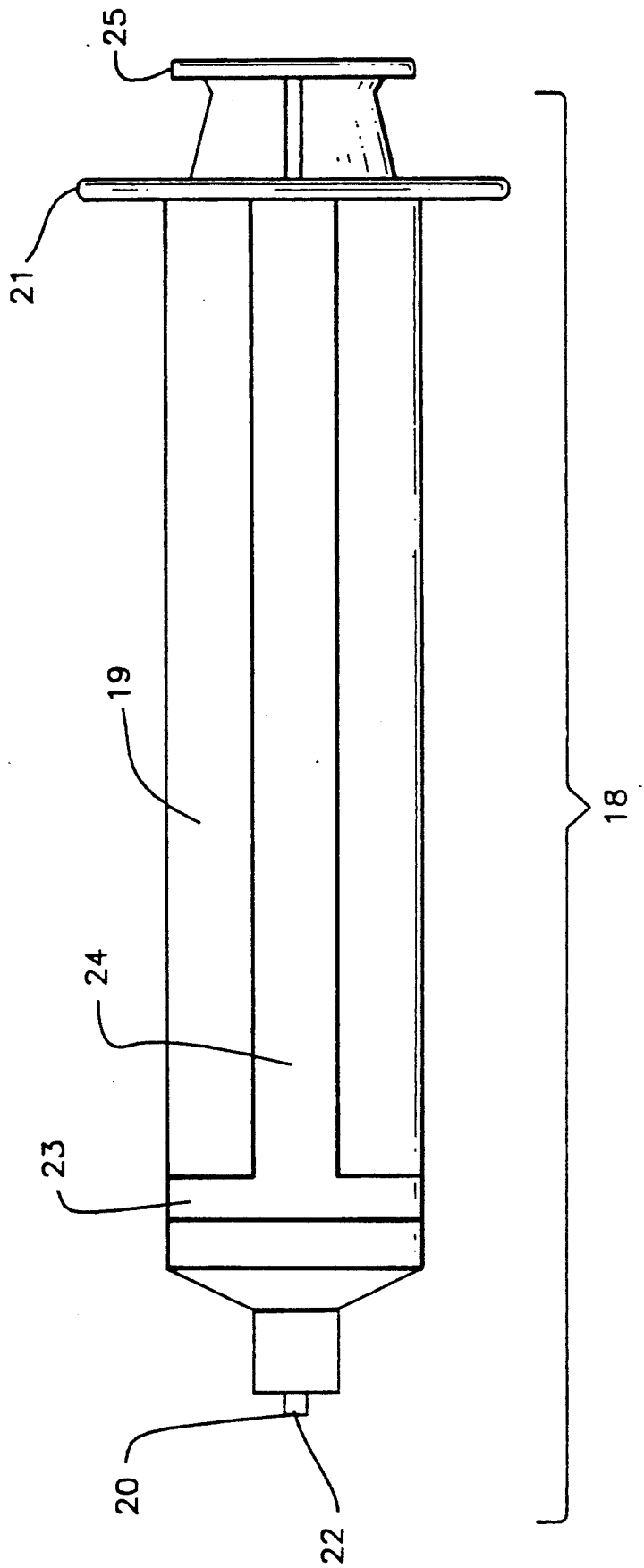
FIG. 3 shows a disposable fluid transfer syringe means constructed in accordance with the invention.

FIG. 3 shows a disposable transfer syringe means 18 having a longitudinal bore 19, a distal end 20, a proximal end 21, a fluid access port 22, a piston 23, a plunger 24, and a handle 25.

Figure 4:
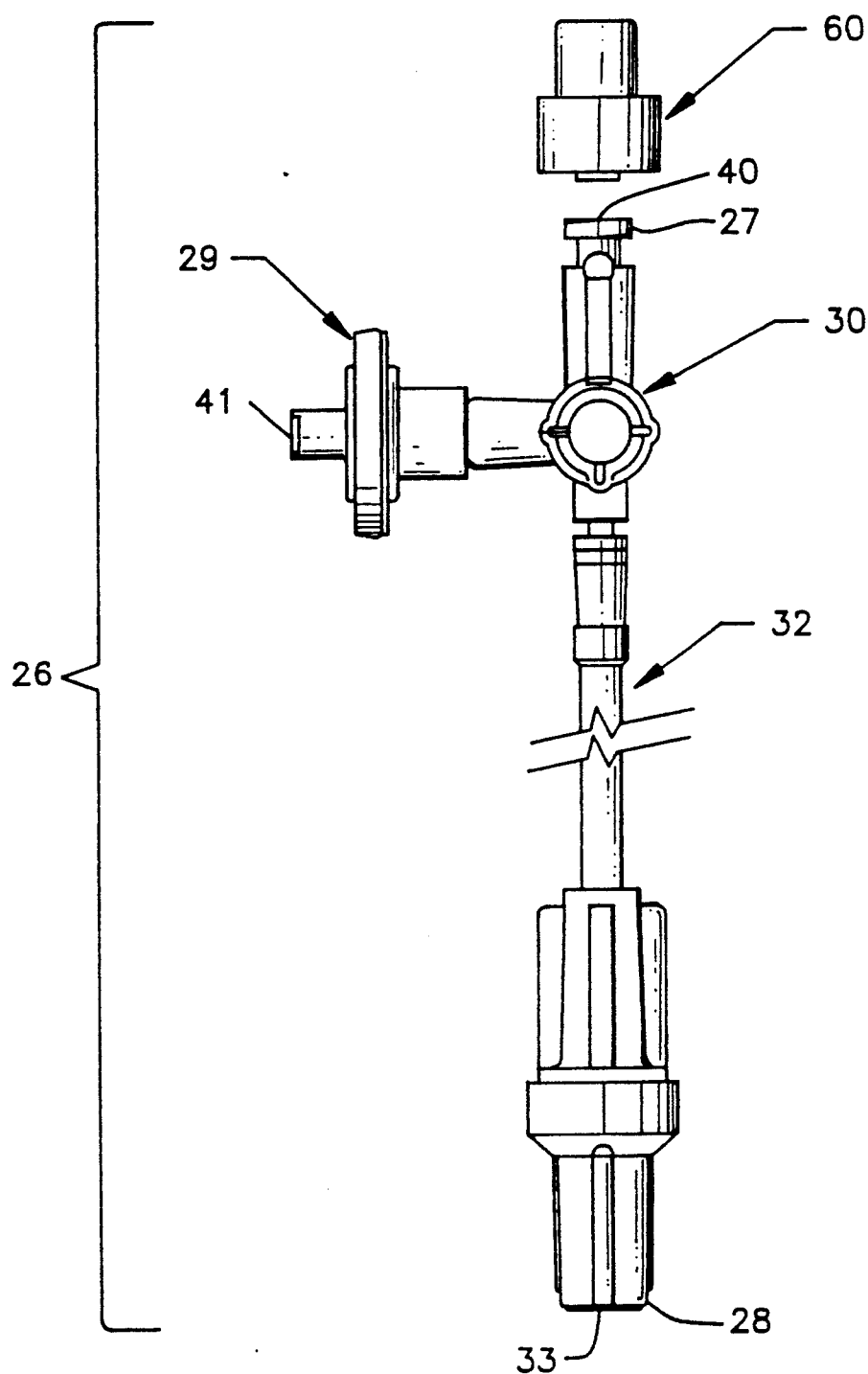
FIG. 4 shows a disposable fluid administration system constructed in accordance with the invention.

FIG. 4 shows a disposable fluid administration system 26 having a proximal end 27, a distal end 28, a filtering means 29, a second fluid control means 30, a fluid conduit 32, a second fluid inlet means 40, a second fluid outlet means 33, an air port 41, and a cap 60.

When the non-pressurized embodiment is utilized, hospital personnel will remove one reusable main supply system 1 (FIG. 1) from a sterilized package. After assuring that first fluid control means 8 is closed, the first fluid inlet means 4 is inserted into a bottle of contrast media or other fluid (not shown) following standard septic and debubbling technique so as to bring the first fluid inlet means 4 in fluid communication with the contrast media or other fluid. In a preferred embodiment, the fluid inlet means 4 is a vented spike. The first fluid control means 8 between said first fluid inlet means 4 and said first fluid outlet means 9 regulates fluid flow between said first fluid inlet means 4 and said first fluid outlet means 9. First fluid control means 8 may be selected from a variety of fluid control means that are well known to those skilled in the art as suitable for this application, however, a stopcock with a sterile cap is preferred. A fluid conduit 7, typically plastic tubing, may be interposed between proximal end 2 and distal end 3 of main supply system 1 as required by specific applications. The bottle containing the contrast media or other fluid is attached to a standard pole for dispensing purposes. A sterile dust cap 10 may be used to cover the first fluid outlet means 9 when the main supply system 1 is not in use. The cap 10 may be flexibly attached to the main supply system 1 so that the cap may be easily located and quickly positioned on the fluid outlet means 9.

A disposable fluid administration system 26 (FIG. 4) is then removed from a sterilized package and is connected to a means (not shown) for introducing the contrast media or fluid into a patient, e.g., a catheter, via the second fluid outlet port 33. A fluid conduit 32, typically plastic tubing, is interposed between the proximal end 27 and distal end 28 of fluid administration system 26 as required by specific applications. The second fluid control means 30 between the second fluid inlet means 40 and the second fluid outlet means 33 regulates the flow of fluid between the second fluid inlet means 40 and the second fluid outlet means 33. A cap 60 may be used to cover second fluid inlet means 40. The second fluid control means 30 may be one of several fluid control means well known to those skilled in the art as suitable for this application, however, a stopcock is preferred.

A sterile transfer means is then removed from a sterile package. The transfer means may be one of several transfer means well known and recognized by those skilled in the art as acceptable for this purpose. In a preferred embodiment, the transfer means is a syringe means 18 as shown in FIG. 3. The distal end 20 of the sterile transfer syringe means 18 is connected to the first fluid outlet means 9 so that fluid access port 22 is in fluid communication with the first fluid outlet means 9. The first fluid control means 8 is opened and fluid is drawn into the transfer syringe means 18 by pulling handle 25 in a direction away from the distal end 20 of transfer syringe means 18. When the transfer syringe means 18 is filled to the desired level, the first fluid control means 8 is closed and the first fluid outlet means 9 is covered by cap 10.

The transfer syringe means 18 is then removed from the main supply system 1 and is transferred to the disposable fluid administration system 26. The distal end 20 of the transfer syringe means 18 is inserted into the second fluid inlet means 40 of disposable fluid administration system 26 so that fluid access port 22 is in fluid communication with the second fluid inlet port 40.

The second fluid control means 30 is then opened and the contents of the transfer syringe means 18 is introduced into and passes through disposable fluid administration system 26 into the patient. The contents of the fluid administration system 26 may be introduced into the patient by several means which are well known to those skilled in the art as suitable for this purpose. In a preferred embodiment, a manifold means or stopcock means in conjunction with an injection syringe means is utilized. If the procedure is complete at this point the entire disposable fluid administration system 26 and the transfer syringe means 18 are disposed of. The main supply system 1 is left tapped in the contrast media or other fluid reservoir for use with the next patient.

If additional contrast media or fluid must be administered the following steps are followed. When the contents in the transfer syringe means 18 is depleted, the transfer syringe means 18 is removed from the disposable fluid administration system 26 and disposed of. A new sterile transfer syringe means 18 is attached to the first fluid outlet port 9 of main supply means 1 as discussed above. The newly filled transfer syringe means 18 is transferred to the second fluid inlet means 40 of disposable fluid administration system 26 and the procedure continues as previously discussed. This disposal, filling, and loading of a plurality of fresh transfer syringe means 18 continues until the treatment is completed.

After the last transfer syringe means 18 is depleted, the second fluid control means 30 on the disposable fluid administration means 26 can be opened to the filtered air port 41. This allows the last of the fluid remaining in disposable fluid administration system 26 to be drained and be administered to the patient, thus, eliminating waste.

On completion of an administration procedure all used components of the fluid administration system 26 and transfer syringe means 18 are disposed of along with the means utilized to connect the disposable fluid administration system 26 to the patient. The main supply system 1 remains tapped in the contrast media or other fluid reservoir for use with the next patient. The fluid outlet means 9 may be capped with sterile protective dust cap 10.

If a pressurizable main supply system 11 (FIG. 2) is utilized, the bottle containing the contrast media or other fluid is pressurized to a nominal pressure by a syringe or other compressed air source via air port 51 of pressurization means 13. The filtering means 16 reduces the likelihood of contaminating the contrast media or fluid when the pressurization medium is introduced via air port 51. The check-valve 17 allows fluid flow from the distal end 15 to the proximal end 14 and prevents fluid flow from the proximal end 14 to the distal end 15 of pressurization means 13. In this embodiment, the first fluid inlet means 50 may be selected from a variety of fluid inlet means well known to those skilled in the art as suitable for this application, however, in a preferred embodiment the fluid inlet means is a vented spike. The first fluid control means 55 may be selected from a variety of fluid control means well known to those skilled in the art as suitable for this application, however, a stopcock with a sterile dust cap is preferred. A sterile dust cap 10' may be used to cover the first fluid outlet means 35 when the pressurizable main supply system 11 is not in use. The cap 10' may be flexibly attached to the pressurizable main supply system 11 so that the cap may be easily located and quickly positioned on the fluid outlet means 35.

The single spiking of a large reservoir of contrast media or other fluid that can be used with several patients results in significant cost savings. Because only one main supply system is used per bottle, the cost for main supply systems is reduced. Also, in contrast to prior art systems wherein the unused fluid remaining after treatment is discarded, Applicant's invention allows the uncontaminated contrast media or other fluid remaining in the reservoir bottle to be saved and used for other patients while significantly reducing the likelihood of accidental cross-contamination from one patient to another.

What is claimed is:

1. An apparatus for supplying a fluid to a patient comprising:
    (a) a main supply means including a longitudinal fluid conduit having a distal end and a proximal end,
       a first fluid inlet means at said proximal end adapted for fluid communication with a fluid source,
       a first fluid outlet means at said distal end adapted for fluid communication with a syringe means and adapted to form a substantially fluid tight seal with a protective cap, and
       a first fluid control means between said first fluid inlet means and said first fluid outlet means for regulating fluid flow between said first fluid inlet means and said first fluid outlet means; and
    (b) a fluid administration means including a longitudinal fluid conduit having a distal end and a proximal end,
       a second fluid inlet means at said proximal end of said fluid administration means adapted for fluid communication with the syringe means,
       a second fluid outlet means at said distal end of said fluid administration means adapted for fluid communication with a means for the delivery of fluid to a patient,
       a second fluid control means between said second fluid inlet means and said second fluid outlet means for regulating the flow of fluid between said second fluid inlet means and said second fluid outlet means and for regulating the flow of air in to and out of said fluid administration means, and
       an air filtering means in fluid communication with said second fluid control means; and
    (c) a syringe means adapted for fluid communication with said first fluid outlet means and said second fluid inlet means.

2. The apparatus of claim 1 further comprising a protective cap adapted to form a substantially fluid tight seal with said first fluid outlet means.

3. The apparatus of claim 1 wherein said first fluid control means is a stopcock.

4. The apparatus of claim 1 wherein said second fluid control means is a stopcock.

5. The apparatus of claim 1 wherein said first fluid inlet means is a vented spike.

6. The apparatus of claim 1 further comprising a pressurization means defining a longitudinal fluid conduit having a distal end and a proximal end, said proximal end of said pressurization means in fluid communication with said first fluid inlet means, said distal end of said pressurization means adapted for fluid communication with a fluid pressurization media,
    a filtering means proximal to said distal end of said pressurization means; and
    a check valve proximal to said filtering means to allow fluid flow toward said proximal end of said pressurization means and to prevent fluid flow toward said distal end of said pressurization means.

* * * * *